United States Patent
Yeh et al.

(10) Patent No.: US 7,329,900 B2
(45) Date of Patent: Feb. 12, 2008

(54) BONDING STRENGTH TESTING DEVICE

(75) Inventors: Chang-Lin Yeh, Kaohsiung (TW); Yi-Shao Lai, Taipei County (TW)

(73) Assignee: Advanced Semiconductor Engineering, Inc., Kaohsiung (TW)

( * ) Notice: Subject to any disclaimer, the term of this patent is extended or adjusted under 35 U.S.C. 154(b) by 213 days.

(21) Appl. No.: 11/306,900

(22) Filed: Jan. 16, 2006

(65) Prior Publication Data

US 2006/0231834 A1    Oct. 19, 2006

(30) Foreign Application Priority Data

Apr. 15, 2005  (TW) .............................. 94111959 A
Nov. 25, 2005  (TW) .............................. 94141426 A

(51) Int. Cl.
*H01L 23/58*    (2006.01)
(52) U.S. Cl. .................. 257/48; 257/738; 257/E21.53; 324/765; 73/842
(58) Field of Classification Search .................. 257/48, 257/E21.53
See application file for complete search history.

(56) References Cited

U.S. PATENT DOCUMENTS 6,564,648 B2 *  5/2003  Lee et al. ..................... 73/842

* cited by examiner

*Primary Examiner*—Tu-Tu V. Ho
(74) *Attorney, Agent, or Firm*—Jianq Chyun IP Office

(57) ABSTRACT

A bonding strength test device suits to perform a bonding strength test for at least one solder ball that fixed on a substrate. The bonding strength test device includes a fixed base and an impact apparatus. The impact apparatus has a first end and a second end corresponding to the first end. While an impact is applied to the first end of the impact apparatus, the impact apparatus moves downward, and the second end of the impact apparatus hits the solder ball on the substrate for performing the bonding strength test. Besides, the fixed base is used for limiting the downward movement of the impact apparatus.

14 Claims, 5 Drawing Sheets

BONDING STRENGTH TESTING DEVICE

CROSS-REFERENCE TO RELATED APPLICATION

This application claims the priority benefit of Taiwan applications serial no. 94111959, filed on Apr. 15, 2005, and serial no. 94141426, filed on Nov. 25, 2005. All disclosure of these Taiwan applications is incorporated herein by reference.

BACKGROUND OF THE INVENTION

1. Field of the Invention

The present invention relates to a bonding strength testing device. More particularly, the present invention relates to a bonding strength testing device for testing the strength of a solider ball.

2. Description of the Related Art

With the rapid progress in electronic technologies, more personalized and functionally powerful electronic products are out in the market. In general, a list of tests needs to be performed on any fully packaged electronic product before shipment. The list of tests for ensuring the yield and quality of the electronic product includes, for example, an aging test, an electrical test, a pull test, a solder ball impact test and so on. Using the solder ball impact test as an example, two types of bonding strength testing devices are commonly deployed by manufacturers to test the bonding strength of solder balls. FIG. 1 is a schematic cross-sectional view of a conventional bonding strength testing device. The method of testing the bonding strength using the bonding strength testing device 100a in FIG. 1 includes raising the swinging pendulum 110 to a height H0 and then letting go of the swinging pendulum 110. The swinging pendulum 110 impacts the solder ball 130 implanted in the substrate 120. When the solder ball 130 breaks away from the substrate 120, a portion of the energy of the swinging pendulum 110 will be absorbed so that the remaining energy permits the swinging pendulum 110 to rise to another height H1 at the other end. Knowing the weight of the swinging pendulum 110 and the difference in height between H0 and H1, the amount of energy needed to break the solder ball 130 can be calculated.

FIG. 2 is a schematic cross-sectional view of another conventional bonding strength testing device. The method of testing the bonding strength using the bonding strength testing device 100b in FIG. 2 includes driving the push rod 140 to a constant speed (for example, about 300 m/s). Then, the push rod 140 impacts the solder ball 130 on the substrate 120 until the solder ball 130 breaks away from the substrate 120. However, this type of bonding strength testing device 100b can analyze the damaging mode of the solder ball 130 only. Furthermore, with the stress sensor 150 and the solder ball 130 separated from each other by a relatively large distance, overall sensitivity of the test is usually poor. Therefore, the stress sensor 150 can hardly obtain an accurate profile of the impact response of the solder ball 130.

SUMMARY OF THE INVENTION

Accordingly, at least one objective of the present invention is to provide a bonding strength testing device suitable for measuring the largest impact force, the continuous impact duration and the ductility of a solder ball in a bonding strength test of the solder ball.

To achieve these and other advantages and in accordance with the purpose of the invention, as embodied and broadly described herein, the invention provides a bonding strength testing device suitable for performing a bonding strength test on at least a solder ball fixed to a substrate. The bonding strength testing device includes a fixed base, a impact apparatus, a displacement sensor and a stress sensor. The fixed base has a through hole and the impact apparatus can slide through the through hole. The impact apparatus has a first end and a second end corresponding to the first end. The first end of the impact apparatus is suitable for receiving an external force so that a bonding strength test of the solder ball can be performed through the transmission of the external force to the second end of the impact apparatus. The displacement sensor is disposed on the fixed base for measuring the relative displacement between the impact apparatus and the fixed base. The stress sensor is disposed on the impact apparatus for measuring the stress applied to the impact apparatus.

According to the bonding strength testing device in the preferred embodiment of the present invention, the fixed base is a first position limiting structure located on the hole wall of the through hole, for example. The impact apparatus has a second position limiting structure disposed in a location corresponding to the first position limiting structure. Furthermore, the sliding distance of the impact apparatus is limited through the mechanical interference between the first position limiting structure and the second position limiting structure. In addition, the first position limiting structure may include a recess structure and the second position limiting structure may include a protruding structure, for example. Alternatively, the first position limiting structure includes a protruding structure and the second position limiting structure includes a recess structure, for example.

According to the preferred embodiment of the present invention, the bonding strength testing device further includes a buffering element disposed on the surface of the first position limiting structure for interfering with the second position limiting structure. Alternatively, the buffering element is disposed on the surface of the second position limiting structure for interfering with the first position limiting structure.

The invention further provides a bonding strength testing device suitable for performing a bonding strength test on at least a solder ball fixed onto a substrate. The bonding strength testing device includes an impact apparatus and a fixed base. The impact apparatus has a first end and a second end relative to the first end. While an impact is applied to the first end of the impact apparatus, the impact apparatus moves downward, and the second end of the impact apparatus hits the solder ball on the substrate for performing the bonding strength test. The fixed base is used for limiting the downward movement of the impact apparatus.

According to the preferred embodiment of the present invention, the bonding strength testing device further includes a stress sensor disposed on the impact apparatus for measuring the stress applied on the impact apparatus.

According to the preferred embodiment of the present invention, the bonding strength testing device further includes a substrate base and a stress sensor. The substrate base is used for setting the substrate. The stress sensor is disposed on the substrate base for measuring the stress applied on the solder ball of the substrate. Moreover, the bonding strength testing device may further include a signal output apparatus connected to the stress sensor for showing the stress variation sensed by the stress sensor.

According to the preferred embodiment of the present invention, the bonding strength testing device further includes a frame, a sliding track and a block. The locations of the fixed base and the impact apparatus are fixed by the frame. The sliding track is disposed on the frame and located above the impact apparatus. The block can slide in the sliding track and contact the first end of the impact apparatus in the bottom of the sliding track. Otherwise, the sliding track may have a fix/release apparatus for fixing/releasing the block.

According to the preferred embodiment of the present invention, the bonding strength testing device further includes an imaging apparatus facing to the contact surfaces between the impact apparatus and the solder ball.

Accordingly, the bonding strength testing device of the present invention has a stress sensor disposed close to the solder ball and even a displacement sensor disposed therein. Hence, the bonding strength testing device is able to obtain the highest impact force, the continuous impact duration and the ductility of a solder ball in a bonding strength test and compute the impact toughness of the solder ball.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
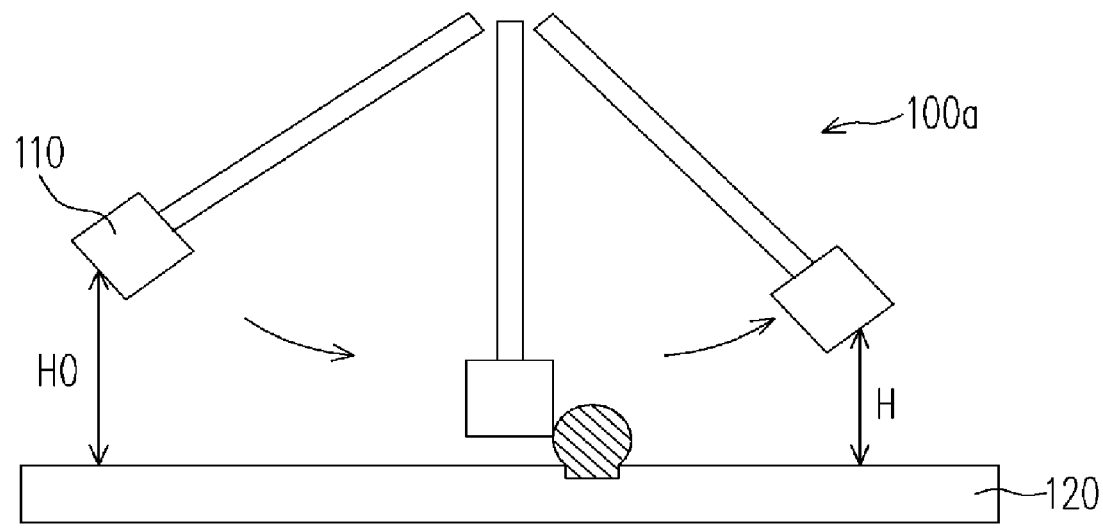
FIG. 1 is a schematic cross-sectional view of a conventional bonding strength testing device.
Figure 2:
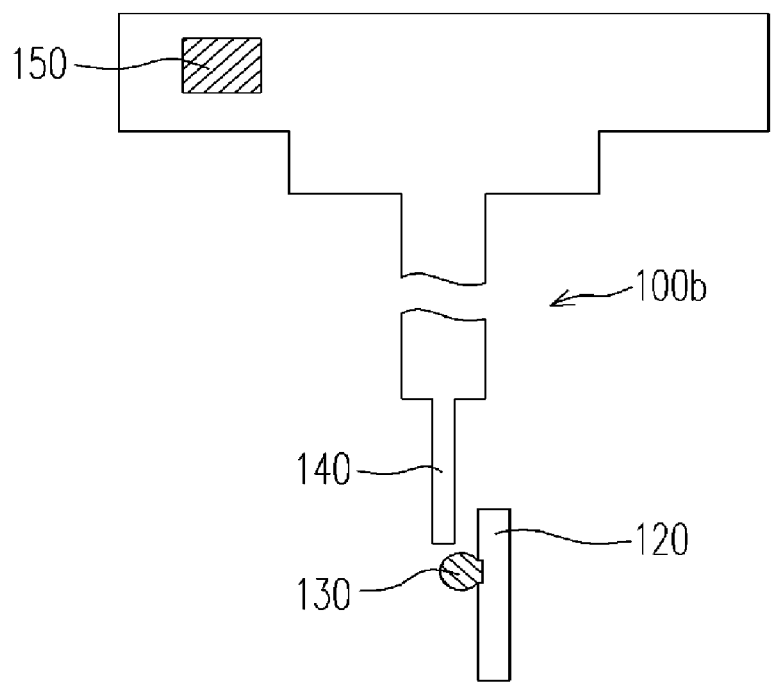
FIG. 2 is a schematic cross-sectional view of another conventional bonding strength testing device.

Reference will now be made in detail to the present preferred embodiments of the invention, examples of which are illustrated in the accompanying drawings. Wherever possible, the same reference numbers are used in the drawings and the description to refer to the same or like parts.

Figure 3:
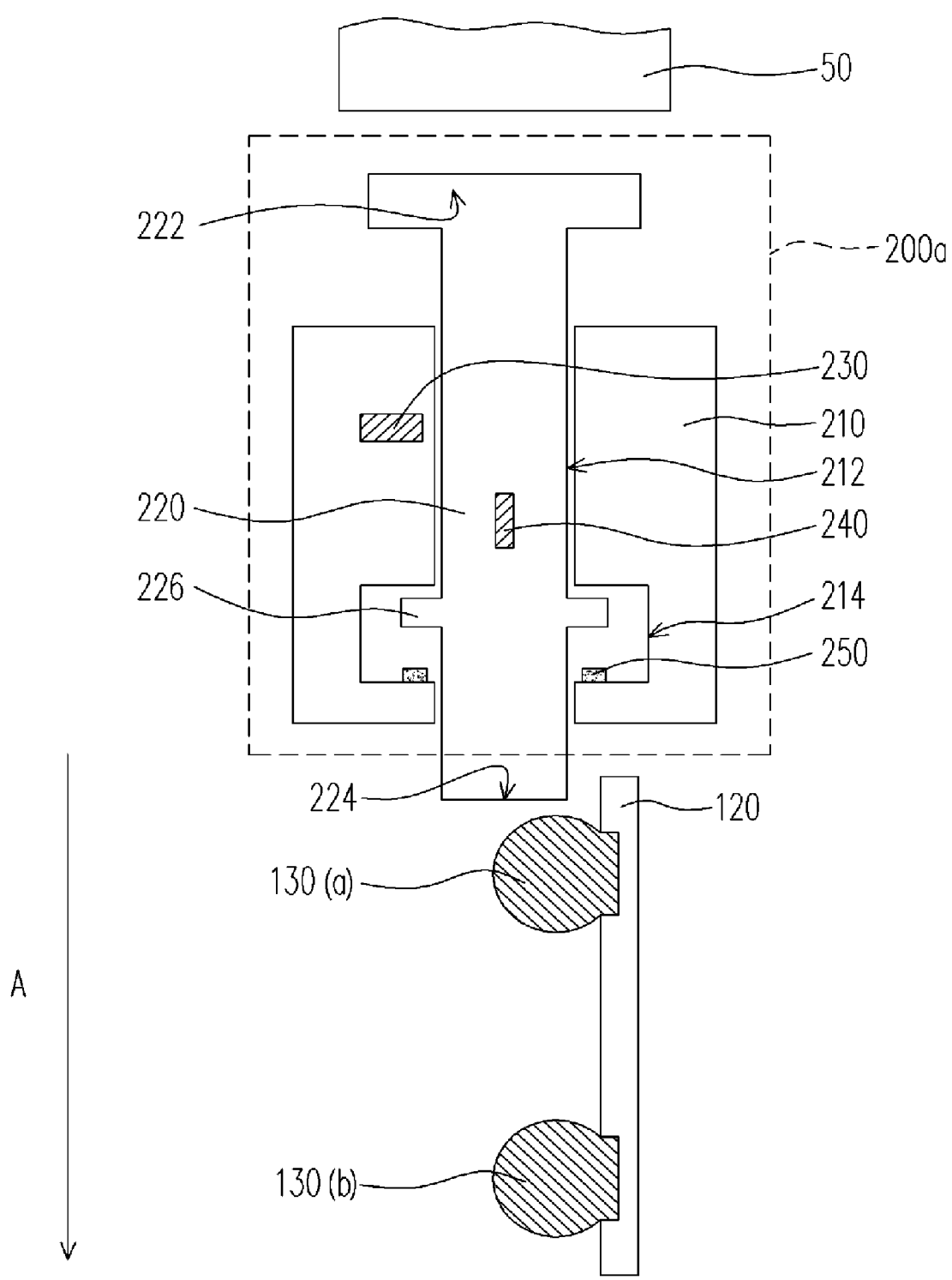
FIG. 3 is a schematic cross-sectional view of a bonding strength testing device according to a first embodiment of the present invention.

FIG. 3 is a schematic cross-sectional view of a bonding strength testing device according to a first embodiment of the present invention. The bonding strength testing device 200a in the present embodiment is suitable for performing a bonding strength test on at least a solder ball 130 fixed on a substrate 120. The substrate 120 is applied to ball grid array (BGA) packaging technique or other packaging techniques that uses solder balls, for example. In other words, the substrate 120 may include a row or multiple rows of solder balls 130. The bonding strength testing device 200a comprises a fixed base 210, a impact apparatus 220, a displacement sensor 230 and a stress sensor 240.

The fixed base 210 has a through hole 212 and the impact apparatus 220 can slide through the through hole 212. The impact apparatus 220 has a first end 222 and a second end 224 relative to the first end 222. The first end 222 of the impact apparatus 220 is designed to receive at external force so that the impact apparatus 222 can apply a force to the solder ball 130 through the second end 224 and carry out the bonding strength test. More specifically, the impact apparatus 220 is shaped into a punching hammer with the first end 222 having a dimension greater than the through hole 212 so that the impact apparatus 220 is prevented from flying off from the fixed base 210.

In addition, the displacement sensor 230 is disposed on the fixed base 210 such as the wall of the through hole 212 for detecting the relative displacement between the impact apparatus 220 and the fixed base 210 during the boding strength test. For example, the displacement sensor 230 measures the amount of displacement by optical means and there are markings or other labels on the corresponding surface of the impact apparatus 220, for example. The stress sensor 240 is disposed on the impact apparatus 220 for measuring the stress on the impact apparatus 220 during the bonding strength test. In other words, the stress sensor 240 measures the reactive force when the solder ball 130 is stressed. Since the stress sensor 240 is disposed in a location very close to the solder ball 130 and the mass of the impact apparatus 220 is close to the solder ball 130, the variation in stress can be accurately measured through the stress sensor 240.

To carry out the bonding strength test, the push rod 50 of a thrust machine (not shown) applies a force to the impact apparatus 220. The method of application of the force includes impacting the first end of the impact apparatus 220 by dropping the push rod 50 from a position high above, pushing the first end 222 of the impact apparatus 220 at a constant speed or some other means. Because the bonding strength testing device 200a in the present embodiment is equipped with a stress sensor 240 and a displacement sensor 230, the impulsive force versus time and the impact distance versus time relationship during a bonding strength test can be registered through the bonding strength testing device 200a. After obtaining the above relationships, the maximum impacting force, the continuous impact duration and the ductility of the solder ball 130 can be computed. Furthermore, by integrating the impact force curve and the increment in impact distance, the impact toughness of the solder ball 130 can be obtained.

In addition, rows of solder balls 130 are normally disposed on the substrate 120. To ensure only a single solder ball 130a is tested by the bonding strength testing device 200a so that the solder ball 130b in the next row is not damaged in a bonding strength test, the sliding distance of the impact apparatus 220 must be limited. To achieve this result, the fixed base 210 in the present embodiment has a first position limiting structure 214, for example. The first position limiting structure 214 is disposed on the wall of the through hole 212. The impact apparatus 220 has a second position limiting structure 226 that corresponds to the first position limiting structure 214, for example. The sliding distance of the impact apparatus 220 is limited by the mechanical interference between the first position limiting structure 214 and the second position limiting structure 226. More specifically, when the first end 222 of the impact apparatus 220 slides in the 'A' direction after receiving a force, the second end 224 of the impact apparatus 220 will impact the solder ball 130. Soon after breaking the solder ball 130 through an impact by the second end 224 of the impact apparatus 220, the second position limiting structure 226 of the impact apparatus 220 contacts first position limiting structure 214 of the fixed base 210. Thus, the impact apparatus 220 is prevented from moving down any further. In the present embodiment, the first position limiting structure 214 could be a recess structure and the second position limiting structure 226 could be a protruding structure, for example. With this design, the undamaged solder ball 130b can become a sample in the next bonding strength test.

After the solder ball 130 is sheared off due to the impact from the second end 224 of the impact apparatus 224, the second position limiting structure 226 of the impact apparatus 220 is in contact with the first position limiting structure 214. In general, the second position limiting structure 226 may break if too large force is applied to the impact apparatus 220 in the bonding strength test of the solder ball 130. Similarly, the contact surfaces between the first position limiting structure 214 and the second position limiting structure 226 may be over-worn due to repeated use. To prevent the breakage of the second position limiting structure 226 and the contact surfaces between the two positioning limiting structures from being over-worn, a buffering element 250 is also included within the bonding strength testing device 200a in the present embodiment. The buffering element 250 is disposed on the surface of the first position limiting structure 214 that contacts the second position limiting structure 226 (as shown in FIG. 3). Alternatively, the buffering element 250 could be disposed on the surface of the second position limiting structure 226 that contacts the first position limiting structure 214 (not shown in FIG. 3). The buffering element 250 is fabricated with rubber material or other buffering material, for example.

It should be noted that the aforementioned first position limiting structure 214 and the second position limiting structure 226 served as an illustration only and should by no means limit the scope of the present invention. Anyone familiar with the technique may provide suitable changes or modification to the position limiting structures when necessary.

Figure 4:
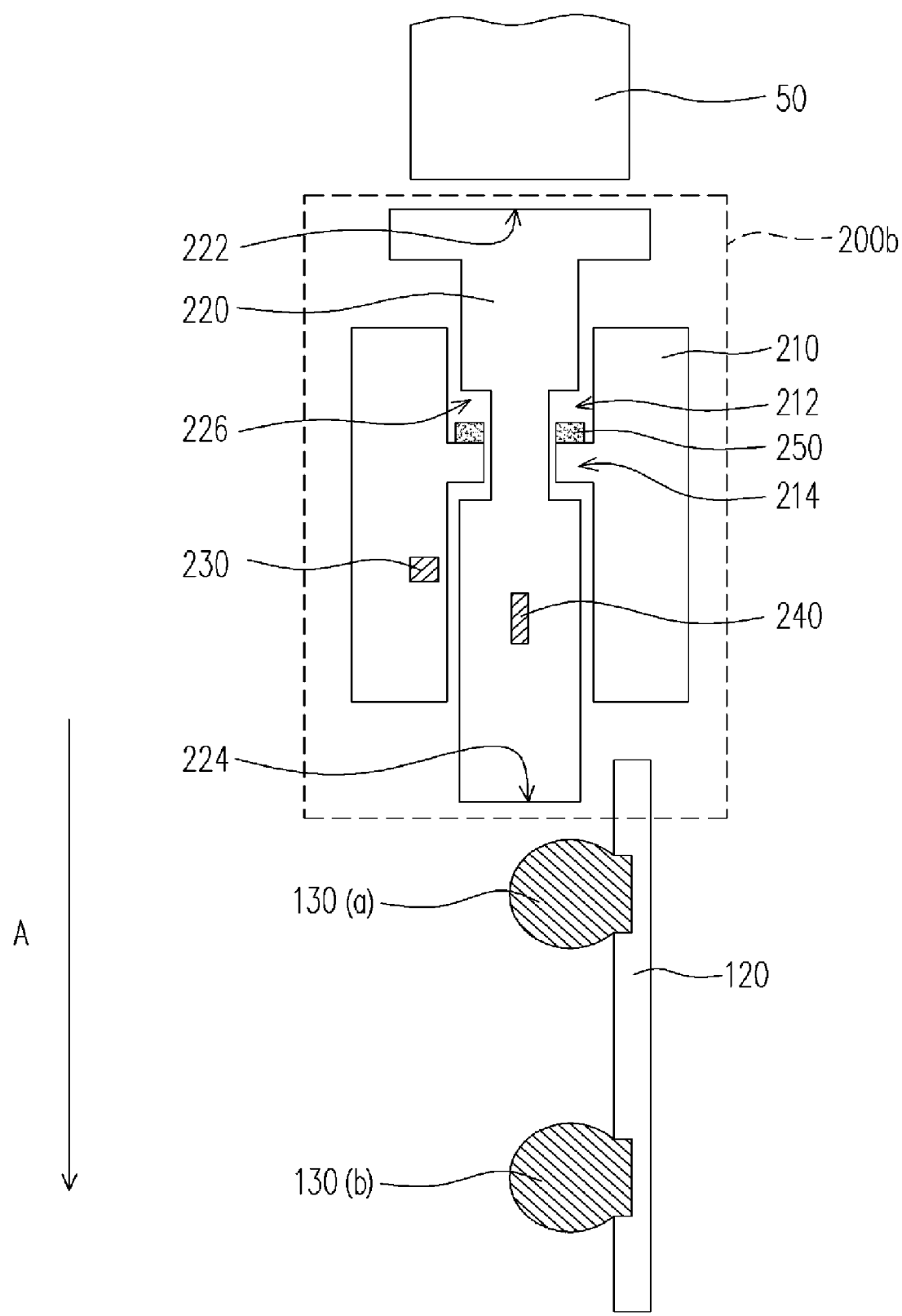
FIG. 4 is a schematic cross-sectional view of a bonding strength testing device according to a second embodiment of the present invention.

FIG. 4 is a schematic cross-sectional view of a bonding strength testing device according to a second embodiment of the present invention. The present embodiment differs from the first embodiment only in that the first position limiting structure 214 is a protruding structure and the second position limiting structure 226 is a recess structure. Since every other aspect of the device is identical to the first embodiment, a detailed description is omitted.

Figure 5:
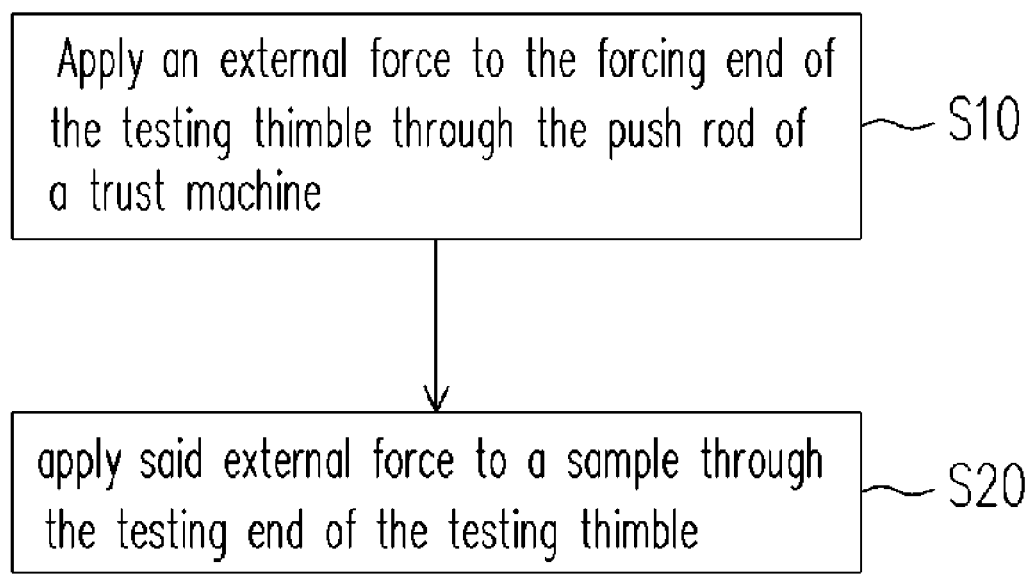
FIG. 5 is a flow diagram showing the steps for performing a bonding strength test according to one embodiment of the present invention.

FIG. 5 is a flow diagram showing the steps for performing a bonding strength test according to one embodiment of the present invention. The bonding strength testing method according to the present embodiment uses the aforementioned bonding strength testing device to perform a bonding strength test on a sample. The sample is a solder ball fixed on a substrate, for example. Obviously, the sample can be other elements whose bonding strength needs to be investigated.

As shown in FIGS. 3 and 5, the bonding strength testing method utilizes the push rod 20 of a trust machine (not shown) to apply an external force on the first end 222 of the impact apparatus 220 in step S10. Thereafter, the external force is applied from the second end 224 of the impact apparatus 220 to the solder ball 130a in step S20 for performing the bonding strength test. In other words, the bonding strength testing method in the present invention transmits an external force to the solder ball 130a through the impact apparatus 220. Furthermore, the stress sensor 240 is disposed in the impact apparatus 220 instead of the more massive push rod 20 having a distance further away from the sample. Thus, the measured impact force versus time relationship is more accurate than the one obtained through the conventional technique. When the bonding strength testing device 200a is additionally equipped with the displacement sensor 230, an impact distance versus time relationship can be obtained from the bonding strength test. Ultimately, information including the maximum impact force, the continuous impact duration, ductility of the solder ball 130a and the impact toughness during the bonding strength test can be obtained.

In addition, in the bonding strength testing method of the present embodiment, the method in which the push rod 50 provides an external force on the impact apparatus 220 includes an impact. In other words, the push rod 50 leaves the impact apparatus 220 immediately after transmitting an external force to the impact apparatus 220 to simulate the condition of the solder ball 130a receiving a dynamic impact. Alternatively, the method in which the push rod 50 provides an external force on the impact apparatus 220 includes a push. That is, the push rod 50 provides a continuous push on the impact apparatus 220 until the solder ball 130a drops off to simulate the conduction of the solder ball 130a receiving a prolonged push.

Figure 6:
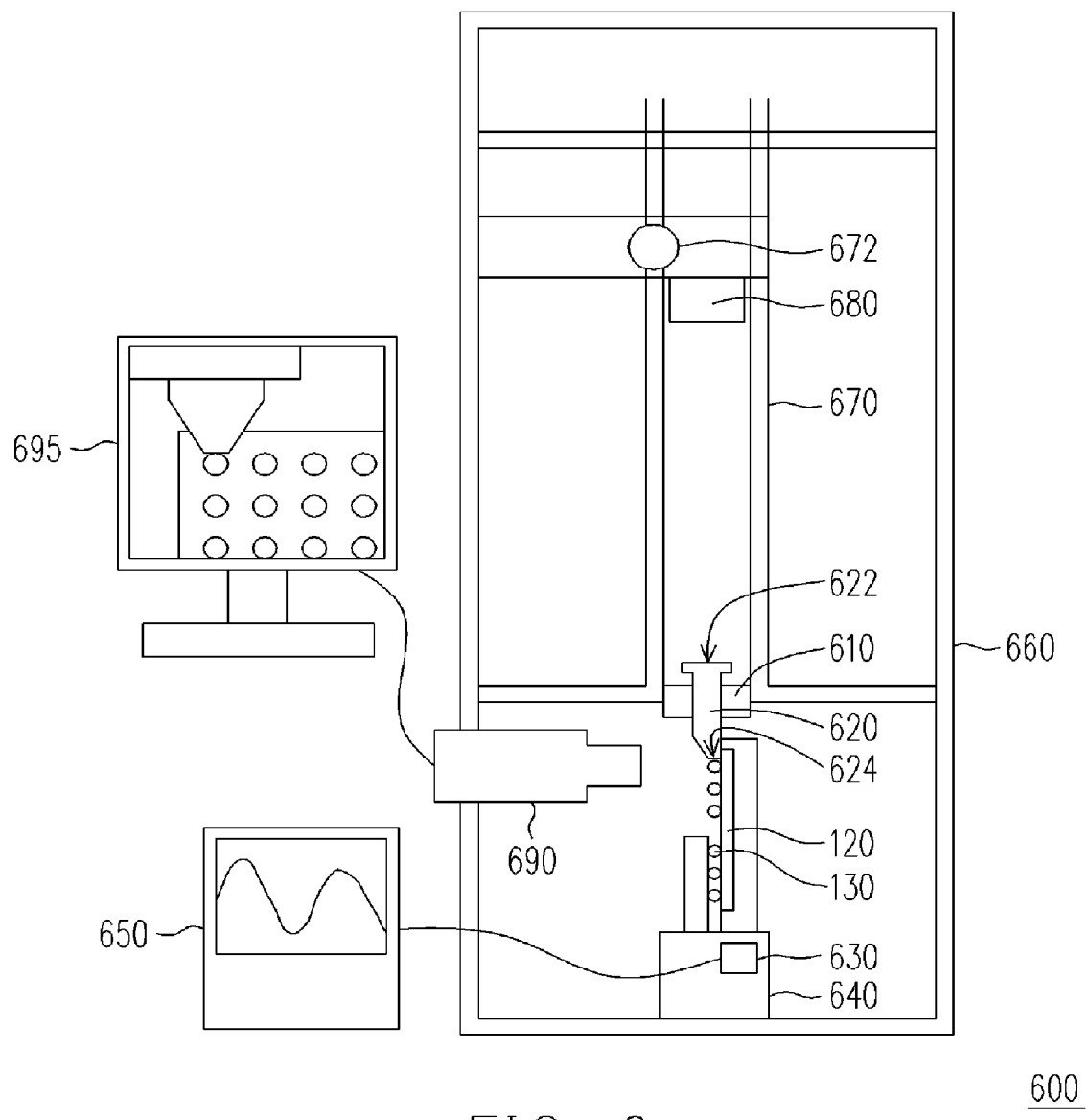
FIG. 6 is a schematic cross-sectional view of a bonding strength testing device according to a third embodiment of the present invention.

FIG. 6 is a schematic cross-sectional view of a bonding strength testing device according to a third embodiment of the present invention. As shown in FIG. 6, the bonding strength testing device 600 according to this embodiment is suitable for performing a bonding strength test on at least a solder ball 130 fixed on a substrate 120. Wherein, the substrate 120 and the solder ball 130 are the same with described above, and the relative introduction is omitted here. The bonding strength testing device 600 includes a fixed base 610 and an impact apparatus 620. The impact apparatus 620 has a first end 622 and a second end 624 relative to the first end 622. While an impact is applied on the first end 622 of the impact apparatus 620, the impact apparatus 260 moves downward, and the second end 624 of the impact apparatus 620 hits the solder ball 130 on the substrate 120 for performing the bonding strength test for the solder ball 130. Wherein, the fixed base 610 is used for limiting the downward moving distance of the impact apparatus 620. Therefore, the impact apparatus 620 is limited to hit several solder balls 130 at once, and the bonding strength test for single solder ball 130 is possible.

Moreover, the bonding strength testing device 600 may further include a stress sensor 630 and a substrate base 640. The substrate base 640 is used for setting the substrate 120. In this embodiment, the substrate 120 is set in vertical on the substrate base 640, and the force provided by substrate base 640 to the substrate 120 is adjustable. The stress sensor 630 is disposed on the substrate base 640 for measuring the stress applied on the solder ball 130 on the substrate 120 during the solder ball 130 impacted by the impact apparatus 620. In another embodiment, the stress sensor 630 could be disposed on the impact apparatus 620.

Moreover, the bonding strength testing device 600 may further include a signal output apparatus 650 connected to the stress sensor 630 for showing the stress variation sensed by the stress sensor 630. For example, the signal output apparatus 650 could be an oscilloscope.

Further, the bonding strength testing device 600 may include a frame 660, a sliding track 670 and a block 680. The frame 660 is used for fixing the locations of the fixed base 610 and the impact apparatus 620. The sliding track 670 is disposed on the frame 660 and located above the impact apparatus 620. The block 680 could slide in the sliding track 670 and contact the first end 622 of the impact apparatus 620 in the bottom of the sliding track 670. Furthermore, the sliding track 670 may have a fix/release apparatus 672 for fixing/releasing the block 680.

Preferably, the bonding strength testing device 600 may further include an imaging apparatus 690 facing the contact surfaces between the impact apparatus 620 and the solder ball 130. The imaging apparatus 690 could be a camera in charge coupled device (CCD) type or other types. Naturally, the imaging apparatus 690 could be connected to a monitor 695 for monitoring the process of the bonding strength test, and the users may adjust the locations of the impact apparatus 620 and the solder ball 130 before test.

For example, the method for using the bonding strength testing device 600 includes fixing the substrate 120 and the solder balls 130 thereon to the substrate base 640 and adjusting the second end 624 of the impact apparatus 620 to the solder ball 130 for test. Thereafter, the block 680 is moved to the desired height. Then, the block 680 is released by the fix/release apparatus 672, and the block 680 falls along the sliding track 670 free and impacts the first end 622 of the impact apparatus 620. Meanwhile, the second end 624 of the impact apparatus 620 hits the solder ball 130 and is stopped by the fixed base 610 after hit one solder ball 130. During the solder ball 130 hitting by the impact apparatus 620, the stress variation sensed by the stress sensor 630 could be shown by the signal output apparatus 650 in time. Final, the maximum impacting force, the continuous impact duration and the ductility of the solder ball 130 in the bonding strength test can be computed from the data measured by the stress sensor 630, the weight of the block 680, the falling height of the block 680, et al.

In summary, the bonding strength testing device of the present invention includes a stress sensor disposed close to the solder ball as well as a displacement sensor. Hence, the bonding strength testing device is able to obtain a highly accurate impact force profile (for example, force/time curve and impact distance/time curve). As a result, the maximum impact force, the continuous impact duration and the ductility of a solder ball in a bonding strength test can be obtained and the impact toughness of the solder ball can be computed. In the meantime, the bonding strength test in the present invention also provides a higher degree of measurement accuracy than the conventional device.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A bonding strength testing device suitable for performing a bonding strength test on at least a solder ball fixed onto a substrate, the bonding strength testing device comprising:
    a fixed base having a through hole;
    an impact apparatus being able to slide through the through hole, wherein the impact apparatus has a first end and a second end relative to the first end, and the first end of the impact apparatus is suitable for receiving an external force so that the impact apparatus can apply an impact force on the solder ball for carrying out the bonding strength test through the second end; and
    a stress sensor disposed in the impact apparatus for measuring the stress applied to the impact apparatus.

2. The bonding strength testing device of claim 1, further including a displacement sensor disposed on the fixed base for measuring the relative displacement between the impact apparatus and the fixed base.

3. The bonding strength testing device of claim 1, wherein the fixed base has a first position limiting structure disposed on the wall of the through hole and the impact apparatus has a second position limiting structure that corresponds to the first position limiting structure such that the sliding distance of the impact apparatus is limited by the mechanical interference between the first position limiting structure and the second position limiting structure.

4. The bonding strength testing device of claim 3, wherein the first position limiting structure includes a recess structure and the second position limiting structure includes a protruding structure.

5. The bonding strength testing device of claim 3, wherein the first position limiting structure includes a protruding structure and the second position limiting structure includes a recess structure.

6. The bonding strength testing device of claim 3, further including a buffering element disposed on the surface of the first position limiting structure for interfering with the second position limiting structure.

7. The bonding strength testing device of claim 3, wherein the device further includes a buffering element disposed on the surface of the second position limiting structure for interfering with the first position limiting structure.

8. A bonding strength testing device suitable for performing a bonding strength test on at least a solder ball fixed onto a substrate, the bonding strength testing device comprising:
    an impact apparatus having a first end and a second end relative to the first end, while an impact is applied to the first end of the impact apparatus, the impact apparatus moves downward, and the second end of the impact apparatus hits the solder ball on the substrate for performing the bonding strength test; and
    a fixed base used for limiting the downward movement of the impact apparatus.

9. The bonding strength testing device of claim 8, further including a stress sensor disposed on the impact apparatus for measuring the stress applied on the impact apparatus.

10. The bonding strength testing device of claim 8, further including:
    a substrate base configured for setting the substrate; and
    a stress sensor disposed on the substrate base for measuring the stress applied on the solder ball of the substrate.

11. The bonding strength testing device of claim 10, further including a signal output apparatus connected to the stress sensor for showing the stress variation sensed by the stress sensor.

12. The bonding strength testing device of claim 8, further including:
    a frame for fixing the locations of the fixed base and the impact apparatus;
    a sliding track disposed on the frame and located above the impact apparatus; and
    a block slides in the sliding track and contacts the first end of the impact apparatus in the bottom of the sliding track.

13. The bonding strength testing device of claim 12, wherein the sliding track has a fix/release apparatus for fixing/releasing the block.

14. The bonding strength testing device of claim 8, further including an imaging apparatus facing to the contact surfaces between the impact apparatus and the solder ball.

* * * * *